United States Patent
Vogt

(10) Patent No.: US 9,927,405 B2
(45) Date of Patent: Mar. 27, 2018

(54) PROCESSING SIGNALS ACQUIRED DURING GUIDED WAVE TESTING

(75) Inventor: Thomas Vogt, Richmond (GB)

(73) Assignee: GUIDED ULTRASONICS LTD., Nottinghamshire (GB)

( * ) Notice: Subject to any disclaimer, the term of this patent is extended or adjusted under 35 U.S.C. 154(b) by 521 days.

(21) Appl. No.: 13/812,384

(22) PCT Filed: Mar. 25, 2011

(86) PCT No.: PCT/GB2011/050614
§ 371 (c)(1),
(2), (4) Date: Mar. 1, 2013

(87) PCT Pub. No.: WO2012/013942
PCT Pub. Date: Feb. 2, 2012

(65) Prior Publication Data
US 2013/0179098 A1    Jul. 11, 2013

(30) Foreign Application Priority Data
Jul. 28, 2010 (GB) .................................. 1012597.9

(51) Int. Cl.
*G01N 29/11* (2006.01)
*G01N 29/44* (2006.01)
(Continued)

(52) U.S. Cl.
CPC ............ *G01N 29/44* (2013.01); *G01N 29/043* (2013.01); *G01N 29/11* (2013.01);
(Continued)

(58) Field of Classification Search
CPC .... G01N 29/4463; G01N 29/46; G01N 29/48; G01N 29/043; G01N 29/11
See application file for complete search history.

(56) References Cited

U.S. PATENT DOCUMENTS 6,092,420 A    7/2000    Kimura et al.
6,624,628 B1 *   9/2003    Kwun .................... G01N 29/11
                                                                   324/240
(Continued)

FOREIGN PATENT DOCUMENTS

EP          1698894        9/2006
GB          716687         10/1954
(Continued)

OTHER PUBLICATIONS

International Search Report and Written Opinion from International application No. PCT/GB11/050614, dated May 5, 2011.
(Continued)

*Primary Examiner* — Toan Le
(74) *Attorney, Agent, or Firm* — Stroock & Stroock & Lavan, LLP

(57) ABSTRACT

Processing signals acquired during guided wave testing A method of processing signals acquired during guided wave testing of an elongate member (2), such as a pipe, in which at least one guided wave (7) is generated in the elongate member, the at least one guided wave is reflected by reflectors (8) in the elongate member and reflected guided waves (9) are detected. The method comprises determining at least one reflection coefficient or a parameter for calibrating a guide wave test in dependence upon reflections from the reflectors which include at least one multiple reflection. The reflections may include a single reflection from a first reflector, a single reflection from a second reflector and a multiple reflection from the first and second reflectors.

22 Claims, 8 Drawing Sheets

(51) Int. Cl.
*G01N 29/04* (2006.01)
*G01N 29/46* (2006.01)

(52) U.S. Cl.
CPC ......... *G01N 29/4463* (2013.01); *G01N 29/46* (2013.01); *G01N 2291/044* (2013.01); *G01N 2291/0425* (2013.01); *G01N 2291/2634* (2013.01)

(56) References Cited

U.S. PATENT DOCUMENTS

| | | | |
|---|---|---|---|
| 7,171,854 | B2* | 2/2007 | Nagashima .......... G01N 29/221 73/612 |
| 2003/0033870 | A1 | 2/2003 | Shah et al. |
| 2004/0216512 | A1 | 11/2004 | Kwun et al. |
| 2006/0203086 | A1* | 9/2006 | Pavlakovic .......... G01N 29/041 348/61 |
| 2007/0225930 | A1 | 9/2007 | Kwun et al. |

FOREIGN PATENT DOCUMENTS

| | | |
|---|---|---|
| JP | 2006071420 | 9/2004 |
| WO | 96/12951 | 5/1996 |
| WO | 2012/013942 | 2/2012 |

OTHER PUBLICATIONS

Great Britain Search Report from Great Britain application No. GB 1012597.9, dated Jan. 24, 2011.
Nishino et al. Highly Sensitive Detection of Defects in Piping Using Multireflecting Guided Wave Energy Trapping Method, The Japan Society of Applied Physics p. 066602-1 to 066602-7, Jun. 21, 2010.

\* cited by examiner

US 9,927,405 B2

PROCESSING SIGNALS ACQUIRED DURING GUIDED WAVE TESTING

CROSS-REFERENCE TO RELATED APPLICATIONS

This application is a national stage application under 35 U.S.C. 371 based on and claiming the benefit of International Application Serial No. PCT/GB2011/050614, filed on Mar. 25, 2011, which claims the benefit of priority from United Kingdom Patent Application No. 1012597.9, filed on Jul. 28, 2010, the entire contents of each of which are incorporated herein by reference.

FIELD OF THE INVENTION

The present invention relates to a method of and apparatus for processing signals acquired during guided wave testing of an elongate member, such as a pipe, tube, rod or rail. The present invention also relates to a method of and apparatus for guided wave testing of an elongate member.

BACKGROUND

Guided wave testing is a non-destructive testing method used to inspect pipework for discontinuities in the wall of a pipe, such as corrosion-type defects and cracks. Reference is made to WO 96 12951 A which describes an apparatus and method for inspecting elongate members and which is incorporated herein by reference.

As with most non-destructive testing methods, a guided wave system typically requires calibration so that the received signal amplitudes can be related accurately to the reflection coefficient of the discontinuity. The reflection coefficient is, among other variables such as guided wave wavelength and mode, related to the shape and dimensions of the discontinuity. The reflection coefficient is therefore regularly used to classify defects in terms of severity with respect to the mechanical integrity of the pipework. In order to size defects or other changes in pipe wall thickness, the reflection coefficient is typically converted, using appropriate conversion functions, into an equivalent pipe wall cross-section change. For example, for a circumferentially-oriented, through-wall thickness notch, when using torsional- or longitudinal-type guided wave modes, the reflection coefficient tends to be linearly related to the circumferential extent of the defect and, therefore, also linearly related to the change in pipe wall cross-section caused by the notch. Reference is made to "Defect detection in pipes using guided waves" by M. J. S. Lowe, D. N. Alleyne, and P. Cawley, Ultrasonics, volume 36, pages 147-154 (1998) which is incorporated herein by reference. The reflection coefficient may also be a function of defect depth and axial length. The reflection coefficient may also be a function of the overall shape of the defect. Thus, the conversion function can take different forms.

The methods of calibration currently available tend either to lack accuracy or to make assumptions which cannot be safely assumed to be true.

The most common way of calibrating the size of guided wave reflections is to observe the reflections from girth welds. A typical girth weld reflects approximately 10 to 20% of the guided wave energy, and other indications can be sized relative to the size of the weld reflection. However, the size of the reflection from a girth weld is influenced by the dimensions of girth weld reinforcement, root penetration, width of the girth weld and pipe wall thickness. Weld reinforcement dimensions are not standardised and the dimensions of the weld reinforcement, the root and the width of the weld can vary significantly even within the same pipeline, resulting in a calibration error when assuming a certain size of reflection.

The direct measurement of the weld reinforcement and width using a specialised gauge or measurement of the pipe circumference at the weld location can improve the calibration using girth weld reflections described above. It can be used to calculate the expected size of the reflection, assuming that the girth weld root has a negligible effect on the size of the reflection. However, the dimensions of the weld can vary significantly even within the same girth weld, particularly reinforcement and root penetration, and can therefore lead to significant errors in the calibration. This method of calibration does not take into account the effect of the girth weld root as it cannot be measured.

Furthermore, the use of girth welds for calibration assumes a non-defective weld. If the girth weld is defective in a way which influences the size of the reflection, then any calibration which assumes a certain size of reflection or which involves directly measuring the girth weld reinforcement and width can lead to a significant error in sizing. An example of an in-service defect in a girth weld which can lead such a calibration error is weld root corrosion. An example of a manufacturing defect is insufficient root-penetration.

Calibration using girth welds cannot be used when there are no girth welds within the range of the guided wave test, when they are not accessible for direct measurement or when the size of the reflections from the girth welds is below the detection threshold of the guided wave system, for example when weld reinforcement has been deliberately removed.

A further calibration method involves measurement of the transmitted signal from one transducer ring to a second transducer ring, the second being installed some distance apart from the first. However, the measurement of a transmitted signal from one transducer ring to the second depends on the coupling strength of the two transducer rings on the pipe and therefore can lead to errors in the calibration if the coupling strengths are not equal. Also, this method requires the use of a second transducer ring and so increases equipment requirements. Moreover, this method may also not be practical where there is limited access for the placing transducer rings on the pipe.

US 2004 0216512 A describes a calibration method based on the change in the size of guided wave amplitudes observed when a clamp is placed on a pipe between a discontinuity and the transducer ring. This method requires the use of clamps and assumes that the clamp causes an observable reduction in the size of the reflection from the discontinuity. The use of the clamps increases inspection time and assumes that an appropriate location is available for placing a clamp. Furthermore, when a pipe is coated, the change in observed reflection amplitudes due to the clamp is unlikely to be significant enough for the calibration to be accurate. Thus, removal of the coating would be required.

Referring to FIGS. 1a and 1b, the importance of correctly sizing a defect or other type of reflector will be explained.

FIG. 1a shows the result of a guided wave test, using 36 kHz torsional mode guided wave, of a test pipe (not shown) having an outer diameter of 219.1 mm, a nominal wall thickness of 8.2 mm, two welds, a defect in the positive direction and a square cut end in the negative direction. The square cut end reflects 100% of the guided wave energy. It provides a reference reflector for a 0 dB distance amplitude correction (DAC) curve, i.e. reflection coefficient equals 1.

Adjusting the weld DAC curves to the peak amplitudes of the welds, assuming the weld reflects −16 dB (i.e. a reflection coefficient of approximately 0.16), which is a typical value when using the torsional mode, the defect reflection coefficient is estimated to be approximately 0.09. However, it can be seen that the 0 dB DAC curve does not approximate the reflection from the cut end.

Referring to FIG. 1b, adjusting the 0 dB DAC curve to the cut end, the weld reflection coefficient is estimated to be 0.11 and the defect reflection coefficient approximately 0.06.

This means that the defect size was, based on the assumption that the weld reflects −16 dB of the guided wave energy, overestimated by 50%.

Overestimating the size of defects can lead to costly false calls and decreased reliability of inspection. Equally, the size of a defect can be underestimated when the weld reinforcement is larger than expected or the wall thickness is thinner than assumed, leading to missed calls and again decreasing the reliability of the inspection.

SUMMARY OF THE INVENTION

The present invention seeks to provide a method of determining the reflection coefficient or a parameter suitable for calibrating a guided wave test (such as the outgoing wave amplitude) more reliably, thereby allowing the test to be better calibrated and, therefore, increase reliability of inspection.

According to a first aspect of the present invention there is provided a method of processing signals acquired during guided wave testing of an elongate member in which at least one guided wave is generated in the elongate member, the at least one guided wave is reflected by reflectors in the elongate member and reflected guided waves are detected, the method comprising determining at least one reflection coefficient or a parameter for calibrating a guide wave test in dependence upon reflections from the reflectors including at least one multiple reflection.

This can be used to provide a more reliable measurement of the reflection coefficient or a parameter suitable for calibrating a guided wave test. The parameter may be an amplitude of a guided wave or a parameter based on reflection coefficient, e.g. the physical size of a reflector.

The reflections may include a single reflection from a first reflector, a single reflection from a second reflector and a multiple reflection from the first and second reflectors.

Determining the at least one reflection coefficient or the parameter for calibrating a guide wave test may comprise determining a reflection coefficient of a first reflector and/or a second reflector or the parameter in dependence upon amplitudes of signals corresponding to a single reflection of a first guided wave from the first reflector, a single reflection of the first or a second guided wave from the second reflector and a multiple reflection of the first or second guided wave from the first and second reflectors.

The at least one guided wave may comprise first and second guided waves, wherein during testing, the first guided wave propagated in a first direction along the elongate member and the second guided wave propagated in a second, opposite direction along the elongate member.

The at least one guided wave may comprise one or more respective pulses and the amplitudes are amplitudes of peaks corresponding to respective reflections of the pulses.

Determining the at least one reflection coefficient may include calculating a reflection coefficient, $R_1$, of a first reflector and/or a reflection coefficient, $R_2$, of a second reflector by dividing the amplitude of a signal corresponding to a multiple reflection of a first or second guided wave from the first and second reflectors by the amplitude of a signal corresponding to the single reflection of the first guided wave from the first reflector and/or the amplitude of a signal corresponding to a single reflection of a first or second guided wave from the second reflector.

Determining the parameter for calibrating a guided wave test may comprise calculating an amplitude, $A_0$, of first and/or second guided waves. Calculating the amplitude $A_0$ may include multiplying the amplitude of a signal corresponding to the single reflection of the first guided wave from a first reflector by the amplitude of a signal corresponding to a single reflection of the first or a second guided wave from a second reflector, and dividing by the amplitude of a signal corresponding to a multiple reflection of the first or second guided wave from the first and second reflectors.

For two reflectors disposed on opposite sides of a transducer ring (or other means for generating and detecting guided waves), determining the at least one reflection coefficient may include calculating a reflection coefficient, $R_1$, of a first reflector and/or a reflection coefficient, $R_2$, of a second reflector, wherein:

$$R_1 = \exp(2\alpha|z_1|)\mathrm{sqrt}(A_{121}/A_2)$$

$$R_2 = \exp(2\alpha|z_2|)\mathrm{sqrt}(A_{121} A_2/(A_1)^2)$$

wherein:
- $A_1$ is a peak value and $z_1$ is the peak position of a peak corresponding to a single reflection of a first guided wave from the first reflector,
- $A_2$ is a peak value and $z_2$ is the peak position of a peak corresponding to a single reflection of a second guided wave from the second reflector,
- $A_{121}$ is a peak value of a peak corresponding to a triple reflection of the first guided wave from, in order, the first reflector, the second reflector and the first reflector, and
- $\alpha$ is an attenuation coefficient having a value zero or a positive non-zero number.

Determining the parameter for calibrating a guided wave test may comprise calculating an amplitude, $A_0$, of first and second guided waves, wherein:

$$A_0 = \mathrm{sqrt}((A_1)^2 A_2/A_{121})$$

wherein:
- $A_1$ is a peak value of a peak corresponding to a single reflection of the first guided wave from a first reflector,
- $A_2$ is a peak value of a peak corresponding to a single reflection of the second guided wave from a second reflector, and
- $A_{121}$ is a peak value of a peak corresponding to a triple reflection of the first guided wave from, in order, the first reflector, the second reflector and the first reflector.

For two reflectors disposed on opposite sides of a transducer ring, determining the at least one reflection coefficient may include calculating a reflection coefficient, $R_1$, of a first reflector and/or a reflection coefficient, $R_2$, of a second reflector, wherein:

$$R_1 = \exp(2\alpha|z_1|)A_{12}/A_2$$

$$R_2 = \exp(2\alpha|z_2|)A_{12}/A_1$$

wherein:
- $A_1$ is a peak value and $z_1$ is the peak position of a peak corresponding to a single reflection of a first guided wave from the first reflector, $A_2$ is a peak value and $z_2$ is the peak position of a peak corresponding to a single reflection of a second guided wave from the second reflector, $A_{12}$ is a peak value of a peak corresponding to a double reflection of the first guided wave from the first reflector and then the second reflector, and α is an attenuation coefficient having a value zero or a positive non-zero number.

The amplitude of a double reflection tends to be larger (e.g. compared to the amplitude of a triple reflection) and so can be identified more easily (e.g. against noise). Also, if a trace based on double reflections (or any other even-numbered reflections) is extracted and plotted, then single reflections do not hinder identification of double reflections unlike triple reflections in a trace based on odd-numbered reflections.

Determining the parameter for calibrating a guided wave test may comprise calculating an amplitude, $A_0$, of first and second guided waves, wherein:

$$A_0 = A_1 A_2 / A_{12}$$

wherein:

$A_1$ is a peak value of a peak corresponding to a single reflection of the first guided wave from a first reflector, $A_2$ is a peak value of a peak corresponding to a single reflection of the second guided wave from a second reflector, and $A_{12}$ is a peak value of a peak corresponding to a double reflection of the first guided wave from the first reflector and then the second reflector.

For two reflectors disposed on the same side of a transducer ring, determining the at least one reflection coefficient may include calculating a reflection coefficient, $R_3$, of a first reflector and/or a reflection coefficient, $R_4$, of a second reflector, wherein:

$$R_3 = 1/\sqrt{A^* + 1}$$

$$R_4 = \exp(2\alpha(|z_4| - |z_3|))\sqrt{A^* + 1} A_4 / (A_3 A^*)$$

wherein:

$A_3$ is a peak value and $z_3$ is the peak position of a peak corresponding to a single reflection of a first guided wave from the first reflector, $A_4$ is a peak value and $z_4$ is the peak position of a peak corresponding to a single reflection of the first guided wave from the second reflector, $$A^* = A_4^2 / (A_3 A_{434}),$$

$A_{434}$ is a peak value of a peak corresponding to a triple reflection of the first guided wave from, in order, the second reflector, first reflector and the second reflector, and α is an attenuation coefficient having a value zero or a positive non-zero number.

Determining the parameter for calibrating a guided wave test may comprise calculating an amplitude, $A_0$, of a first guided wave, wherein:

$$A_0 = \exp(2\alpha|z_3|) A_3 \sqrt{A^* + 1}$$

wherein:

$A_3$ is a peak value and $z_3$ is the peak position of a peak corresponding to a single reflection of the first guided wave from a first reflector, $A_4$ is a peak value and $z_4$ is the peak position of a peak corresponding to the single reflection of the first guided wave from a second reflector, $$A^* = A_4^2 / (A_3 A_{434}),$$

$A_{434}$ is a peak value of a peak corresponding to a triple reflection of the first guided wave from, in order, the second reflector, the first reflector and the second reflector, and α is an attenuation coefficient having a value zero or a positive non-zero number.

The reflection coefficient can be determined in this way when reflectors are located on the same side of a transducer ring. This scenario may be less common, but can still arise nevertheless.

A first reflector used to determine the reflection coefficient or parameter can be located outside the dead zone or near field and a second reflector can be located inside the dead zone or near field.

Thus, multiple reflections can be used to detect and size features which could not otherwise be detected or sized.

The method may further comprise fitting at least one distance amplitude correction (DAC) curve to the amplitude of the signal corresponding to the single reflection of a first guided wave from the first reflector and/or the amplitude of the signal corresponding to the single reflection of a first or second guided wave from the second reflector, and/or to a parameter for calibrating the guided wave test, for example $A_0$.

The method may further comprise sending signals to at least two sets of transducers spaced apart along the elongate member, receiving signals from at least two sets of transducers spaced apart along the elongate member, and extracting signal contributions corresponding to even-numbered reflections, for example, using Fast Fourier transform processing in the frequency domain.

The method may comprise displaying a plot using the extracted signal contributions.

According to a second aspect of the present invention there is provided a method comprising generating the at least one guided wave in an elongate member, acquiring signals from transducers coupled to the elongate member and processing the signals.

According to a third aspect of the present invention there is provided a method of guided wave testing of an elongate member in which at least one outgoing wave is generated in and propagates along the elongate member, the at least one guided wave is reflected by reflectors in the elongate member and reflected guided waves are detected by at least two sets of transducers spaced apart along the elongate member, the method comprising receiving signals from the at least two sets of transducers, identifying signal contributions corresponding to even-numbered reflections and extracting the signal contributions.

The method may comprise displaying a plot using the extracted signal contributions.

According to a fourth aspect of the present invention there is provided a computer program which, when executed by a computer, causes the computer to perform the method.

According to a fifth aspect of the present invention there is provided a computer-readable medium storing the computer program. The computer-readable medium may be non-transitory.

According to a sixth aspect of the present invention there is provided an apparatus, for example comprising a computer including at least one processor and memory, configured to perform the method.

The apparatus may further comprise transducers for generating at least one guided wave in an elongate member and instrumentation for generating a set of signals for driving the transducers and receiving signals generated by the transducers.

The computer and the instrumentation may be provided by a single unit, e.g. the instrumentation.

BRIEF DESCRIPTION OF THE DRAWINGS

Certain embodiments of the present invention will now be described, by way of example, with reference to FIGS. 2 to 10b of the accompanying drawings in which:

FIG. 4a illustrates propagation of guided waves in a pipe in which a guided wave is reflected multiple times between two reflectors and the reflections are received from the same side of the pipe into which the outgoing waves are sent;

FIG. 4b schematically illustrates a plot of signal amplitude against distance for the reflected waves shown in FIG. 4a;

FIG. 5a illustrates propagation of guided waves in pipe in which a guided wave is reflected multiple times between two reflectors and the reflections are received from the opposite side of the pipe into which the outgoing waves are sent;

FIG. 5b schematically illustrates a plot of signal amplitude against distance for the reflected waves shown in FIG. 5a;

FIG. 10a illustrates propagation of guided waves in pipe in which a guided wave is reflected multiple times between two reflectors on the same side of a transducer ring; and FIG. 10b schematically illustrates a plot of signal amplitude against distance for the reflected waves shown in FIG. 10a.

DETAILED DESCRIPTION OF CERTAIN EMBODIMENTS

Figure 1:
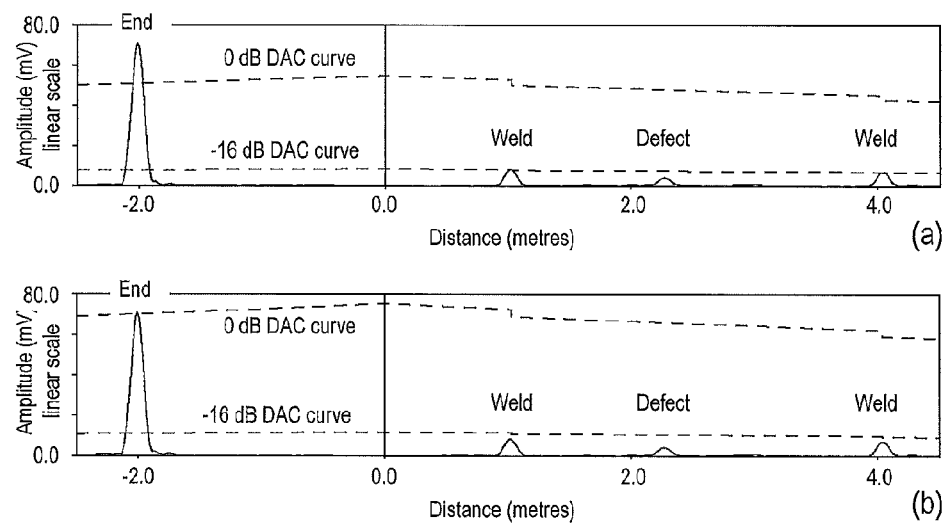
FIG. 1a is a plot of pulse-echo signal amplitude against distance for test of a pipe having a square end cut, two welds and a defect including 0 dB and −16 dB distance amplitude correction (DAC) curves fitted to the peak amplitude of the peak corresponding to reflection from the weld.
FIG. 1b is the same plot as that shown in FIG. 1a but which includes 0 dB and −16 dB DAC curves fitted to the peak amplitude of the peak corresponding to reflection from the square cut end.
Figure 2:
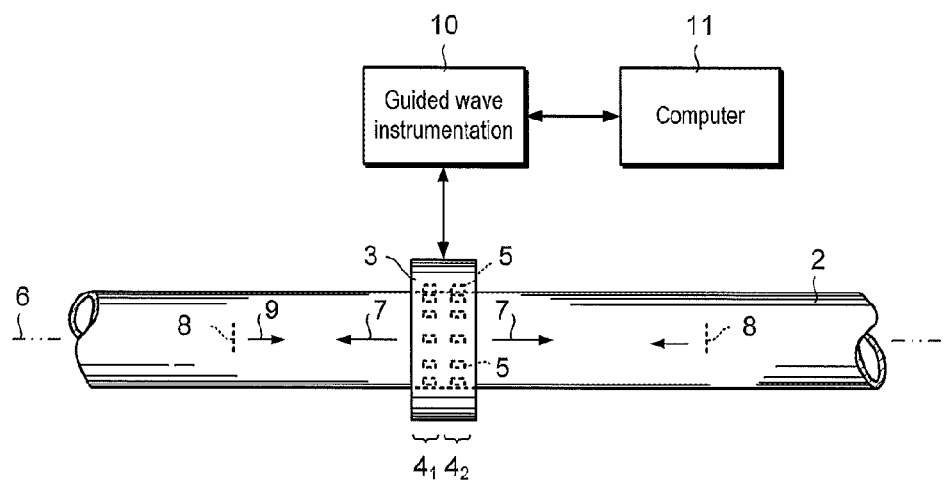
FIG. 2 illustrates a guided wave inspection system in accordance with the present invention.

Referring to FIG. 2, a system 1 for inspecting a pipe 2 or other elongate member using guided waves is shown. The system 1 includes a transducer ring 3 having at least two rows or sets $4_1$, $4_2$ of transmitting/receiving transducers 5 spaced apart along the longitudinal axis 6 of the pipe 2. In this example, the transducers 5 are discrete, piezoelectric transducers and the transducers 5 in each set $4_1$, $4_2$ are angularly-spaced around the perimeter of the pipe 2 in a similar way to that described in WO 96 12951 A ibid. However, the transducers 5 need not be discrete and other types of transducers can be used.

The transducer ring 3 is used to excite guided waves 7 in the form of pulses in the pipe 2 at a propagating frequency, typically in the range between about 10 and about 500 kHz, which propagate along the pipe 2. Discontinuities 8, such as defects, welds or other types of interface (herein collectively referred to as "reflectors") reflect some or all of the outgoing waves 7 as reflected waves 9. At least two sets $4_1$, $4_2$ of transducers 5 are used so that the direction of propagation of reflected waves 9 can be determined. As will be explained later, an outgoing wave 7 can be reflected once, twice, three times or more. Moreover, a wave 7 which is multiply reflected between a pair of reflectors 8 can be used to help determine the size of reflectors 11 more accurately. Reflected waves 9 are recorded in pulse-echo and pitch-catch arrangements using the sets of transducers controlled by guided wave instrumentation 10 and a computer 11. The guided wave instrumentation 10 is a microprocessor-controlled system which sends electrical signals in the form of tone bursts (or "wavepackets") to the transducers 5 in the transducer ring 3. The transducers 5 convert the electrical signals into mechanical vibrations and excite guided waves 7 in the pipe 2. The transducers 5 also convert the mechanical vibration of reflected waves 9 into electrical signals which are fed to the guided wave instrumentation 10 where they can be amplified and/or filtered and digitised. The electrical signal is a function of the mechanical vibrations. The guided wave instrumentation 10 and/or computer 11 can record the electrical signals and can process the signals to select waves of a given directionality and/or modes. For example, this may involve filtering out or subtracting contributions to a signal from unwanted reflections and/or modes. The instrumentation 10 or computer 11 can convert a time-varying electrical signal which can include contributions from different reflections into an amplitude-distance plot using the equation z=v·t/2 where v, is the velocity of the guided wave, t is time and z is distance. The signal trace is often referred to as an "A-scan type" plot and shows the envelope of the rectified electrical signal.

Referring also to FIG. 2, the computer system 11 is shown in more detail. The computer system 11 includes one or more processors 21, memory 22 and an input/output (I/O) interface 23 operatively connected by a bus 24. The I/O interface 23 is operatively connected to, among other things, an instrumentation interface 25, a display 26 (which can take the form of a touch screen), user input device(s) 27 (such as a keyboard and a pointing device or touch screen), and storage 28 (for example in the form of a hard disk drive or non-volatile memory).

Computer program code 29 is held in storage 28 and loaded into memory 22 for execution by the processor 21.

The computer system 11 carries out a sizing and calibration method based on parts or components of the signals received from the transducers 5 corresponding to reflections from the reflectors which include multiple reflections between reflectors. In particular, the method is based on parts or components of the signals received from the transducers 5 corresponding to single reflections received from one or both of two reflectors and a multiple reflection received after reverberating between the two reflectors. In this example, the amplitudes of peaks corresponding to reflected pulses are used. Using the amplitude of the peak corresponding to a reflection from a first reflector, the amplitude of the peak corresponding to a reflection from a second reflector, and the amplitude of the peak corresponding to a multiple reflection between the first and the second reflectors, the sizes of the two reflectors can be determined. This can be further used to determine the size of other reflectors either by calculation or by using distance amplitude correction (DAC) curve(s).

The calibration method provides a way of sizing guided wave signals without the use of artificially-introduced attachments, such as clamps. Nevertheless, clamps can be used to create a reflection for sizing purposes. The use of clamps can be helpful if no significant reflectors can be observed.

In the following, sizing and calibration methods are described which employ signals arising from two reflectors 8 located on opposite sides of the transducer ring 3. Generally, this arrangement occurs most often and the reflections are most easily observed. However, the methods can be based on reflections received from reflectors 8 that are both located on only one side of the transducer ring 3.

Sizing and calibration methods can be based on double or triple reflections.

Figure 4:
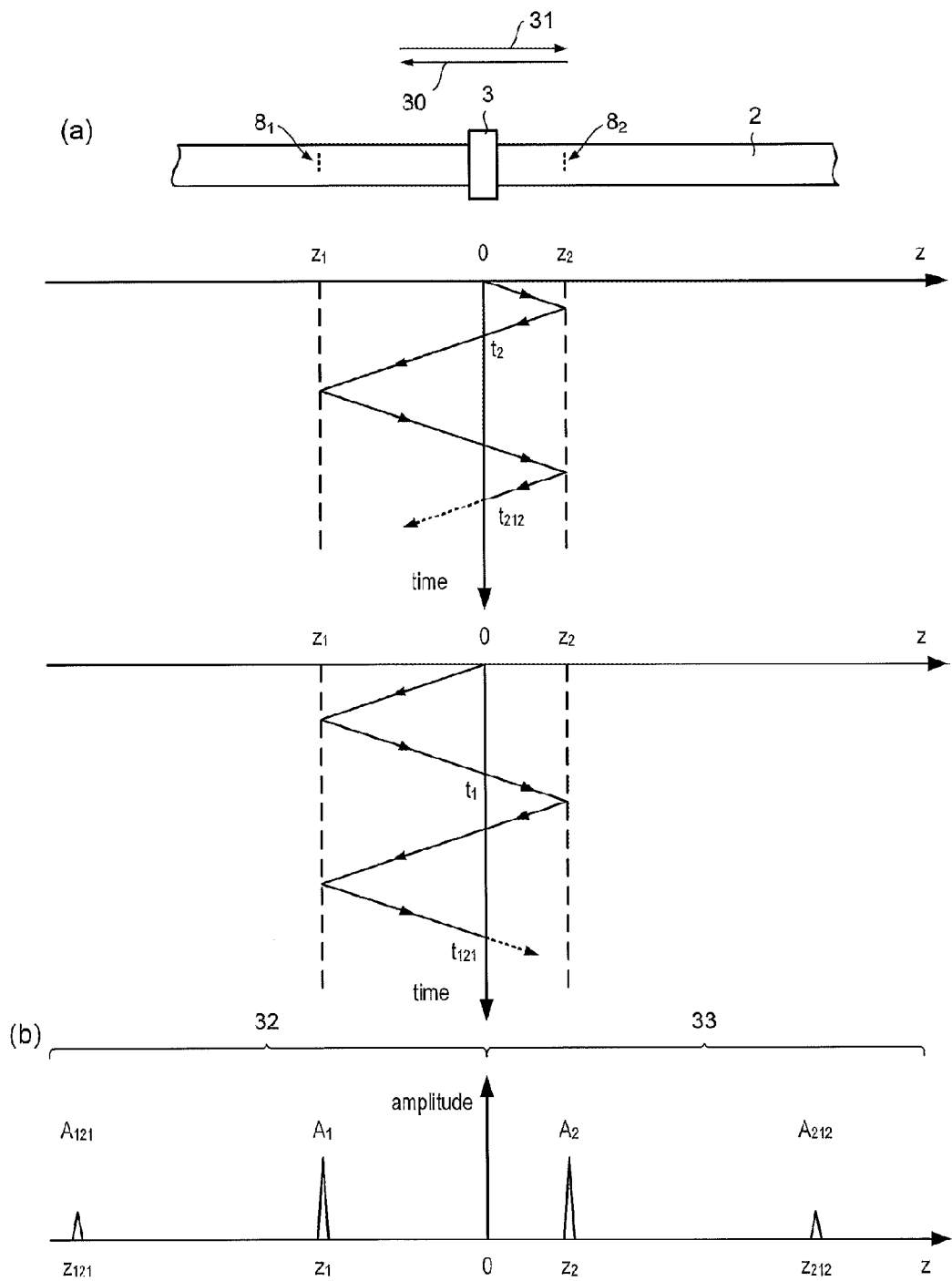

Referring to FIG. 4$a$, the pipe 2 is shown having first and second reflectors $8_1$, $8_2$ located on opposite sides of the transducer ring 3. The transducer ring 3 is used to excite a first guided wave in the form of a pulse which propagates backwards 30 (shown here to be along the negative z direction) along the pipe 2 and a second guided wave in the form of a pulse which propagates forwards 31 having the same amplitude. The guided waves are reflected by the reflectors 8 and the reflected waves are detected by the transducer ring 3.

The transducer ring 3 receives first and second direct pulse-echo (i.e. single reflections) reflected from the first and second reflectors $8_1$, $8_2$ respectively and having paths z: $0 \rightarrow -z_1 \rightarrow 0$ and z: $0 \rightarrow z_2 \rightarrow 0$. The first and second direct pulse-echoes have peak amplitude values $A_1$ and $A_2$ respectively.

The transducer ring 3 receives a first triple-reflection which has been reflected first by the first reflector $8_1$, then by the second reflector $8_2$ and then again by the first reflector $8_1$, i.e. a path z: $0 \rightarrow -z_1 \rightarrow z_2 \rightarrow z_1 \rightarrow 0$. In this case, the measured signal has a peak amplitude $A_{121}$ and corresponds to a reflection received by the transducer ring 3 from the direction of the first reflector $8_1$.

The transducer ring 3 also receives a second triple-reflection which has been reflected by the second reflector $8_2$, then by the first reflector $8_1$ and then again by the second reflector $8_2$, i.e. a path z: $0 \rightarrow z_2 \rightarrow -z_1 \rightarrow z_2 \rightarrow 0$. In this case, the measured signal has a peak amplitude $A_{212}$ and corresponds to a reflection received by the transducer ring 3 from the direction of the second reflector $8_2$.

FIG. 4$b$ is an amplitude—distance plot showing peaks in amplitude corresponding to odd-numbered reflections, in particular single and triple reflections. The characteristic distances at which the peaks appear can be used to identify reverberation echoes.

Figure 5:
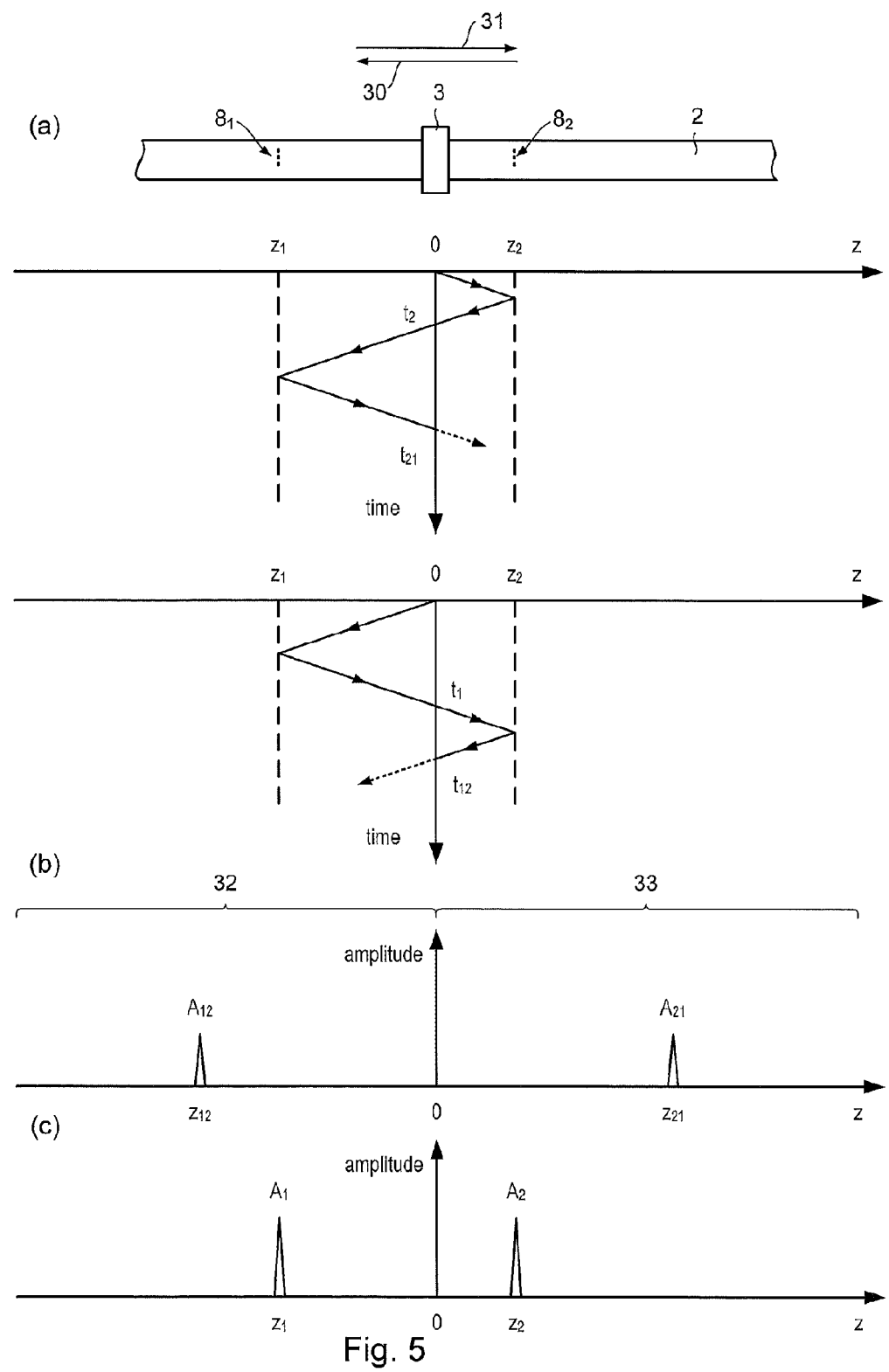

Referring to 5$a$, the same pipe 2 is shown. FIG. 5$a$ differs from FIG. 4$a$ in that instead of odd-numbered reflections, even-numbered reflections, in particular double reflections, are shown. However, single reflections are also used when calculating reflection coefficients.

The transducer ring 3 receives a first double-reflection which has been reflected first by the first reflector $8_1$ and then by the second reflector $8_2$, i.e. a path z: $0 \rightarrow -z_1 \rightarrow z_2 \rightarrow 0$. In this case, the measured signal has a peak amplitude $A_{12}$ and corresponds to a reflected wave received by the transducer ring 3 from the opposite direction of the first reflector $8_1$.

The transducer ring 3 also receives a second double-reflection which has been reflected by the second reflector $8_2$ and then by the first reflector $8_1$, i.e. a path z: $0 \rightarrow z_2 \rightarrow -z_1 \rightarrow 0$. In this case, the measured signal has a peak amplitude $A_{21}$ and corresponds to a reflected wave received by the transducer ring 3 from the opposite direction of the second reflector $8_2$.

FIG. 5$b$ is an amplitude—distance plot showing peaks in amplitude corresponding to double reflections. FIG. 5$c$ is an amplitude—distance plot showing peaks corresponding to single reflections.

The plot shown in FIG. 5$b$ is obtained by taking into account the directions in which outgoing and reflected waves propagate and extracting signal contributions arising from an even number of reflections. The guided wave instrumentation 10 (FIG. 2) and/or the computer system 11 (FIG. 2) can process the signals received from two or more rings of transducers $4_1$, $4_2$ (FIG. 2) to produce a signal trace having peaks which arise from an outgoing wave propagating in one direction, i.e. sent out into one side of the transducer ring, and waves propagating in the same direction received on the opposite side of the transducer ring 3 (FIG. 2) and vice versa. Thus, the plot shows peaks arising from double and (if detectable) other even-numbered reflections, but not from odd-numbered reflections such as single and triple reflections. Therefore, this type of plot only shows peaks arising from even-numbered reverberations (i.e. there are no single reflections) and so this type of plot is herein referred to as a "reverberation plot". The plot is characterised by being symmetrical about the origin (i.e. z=0). Thus, in some embodiments, only one side of the trace need be plotted.

Referring in particular to FIG. 5$b$, the negative and positive sides 32, 33 of the plot shown in FIG. 5$b$ can be obtained in a several different ways. The negative side 32 of the plot (i.e. z≤0) can be obtained by generating a pulse in the pipe 2 propagating in a negative (or "backwards") direction 30, for example, by driving two transducer rings $4_1$, $4_2$ (FIG. 2) with appropriate phase difference and detecting reflected pulses propagating in the same direction (i.e. backwards) by measuring phase difference or time delay between the signals received from the two transducer rings $4_1$, $4_2$ (FIG. 2). Likewise, the positive side 33 of the plot (i.e. 0≤z) can be obtained by generating pulses in the pipe propagating in the positive direction 31 and detecting the reflected pulses propagating in a positive direction 31. The guided wave instrumentation 10 and/or computer system 11 processes the signals to identify contributions or components (in this case peaks) corresponding to forward and backward propagating pulses and extract only those contributions or components attributable to even-numbered reflections.

In particular, using two sets of transceivers $4_1$, $4_2$, extraction is achieved using first and second pulse-echo traces (in which a transducer set excites the outgoing wave and the same transducer set detects the reflection) for the first and second transducer sets $4_1$, $4_2$ and one pitch-catch trace (in which one transducer set excites the outgoing wave and another transducer set detects the reflection). Each measured trace comprises a different mixture of three independent component traces corresponding to reflections travelling in forward and reverse directions arising from outgoing pulses travelling in forwards and reverse directions.

The traces are processed using fast Fourier transforms in the frequency domain to solve three unknowns (i.e. component traces), namely a first component trace corresponding to pulses transmitted in the forward direction and reflected pulses received propagating in the opposite direction (i.e. backwards), a second component trace corresponding to pulses transmitted in the backward direction and reflected pulses received propagating in the opposite direction (i.e. forwards), and a third component trace corresponding to pulses transmitted in one direction (e.g. forwards) and reflected pulses received propagating in the same direction (e.g. in the case of forward transmitted pulses, the received reflected waves also propagate forwards). Thus, the third component trace corresponding to forward- (or backward-) going transmitted pulses and forward- (or reverse-) going reflections can be extracted and used as a reverberation plot.

Methods based on double reflections are generally preferred because the use of double reflections tends to avoid interference of the double reflection with other reflections. For example, when welds are equally spaced, triple reflections can interfere with a weld reflection and so may not be observed. Furthermore, the signal-to-noise ratio of a double reflection signal tends to be better than a triple reflection signal because it involves fewer reflections.

However, methods based on triple reflections are simpler from the point of view that signals can be sent out in one direction and reflected signals are received from the same direction. When double reflections are used, signals are sent out in one direction and reflections are received from both directions, thus requiring more complex signal processing.

Referring also to FIG. 2, the transducer ring 3 picks up and converts mechanical signals into electrical signals which can be filtered, amplified and pre-processed by the guided wave instrumentation 10 and output as time traces to the computer system 11. The computer system 11 can then be used to size the reflectors and to calibrate signals.

Sizing Reflectors

First, sizing of reflectors based on triple reflections will be described.

The reflection coefficients $R_1$ and $R_2$ for first and second reflectors can be calculated as follows. The amplitudes $A_1$, $A_2$, $A_{121}$ and $A_{212}$ can be expressed as:

$$A_1 = A_0 R_1 \exp(-2\alpha |z_1|) \tag{1-1}$$

$$A_2 = A_0 R_2 \exp(-2\alpha |z_2|) \tag{1-2}$$

$$A_{121} = A_0 (R_1)^2 R_2 \exp(-2\alpha \{2|z_1| + |z_2|\}) \tag{1-3}$$

$$A_{212} = A_0 (R_2)^2 R_1 \exp(-2\alpha \{|z_1| + 2|z_2|\}) \tag{1-4}$$

where is $\alpha$ an attenuation factor which can be zero or a positive non-zero number (i.e. $0 \leq \alpha$) and $A_0$ is the amplitude of the outgoing wave.

Equations (1-1), (1-2) and (1-3), for example, can be re-arranged as:

$$R_1 = \exp(2\alpha |z_1|) \mathrm{sqrt}(A_{121}/A_2) \tag{1-5}$$

$$R_2 = \exp(2\alpha |z_2|) \mathrm{sqrt}(A_{121} A_2 / (A_1)^2) \tag{1-6}$$

$$A_0 = \mathrm{sqrt}((A_1)^2 A_2 / A_{121}) \tag{1-7}$$

Equations (1-1), (1-2) and (1-4) can be re-arranged in a similar way.

The reflection coefficient $R_1$ (and/or $R_2$) for the first and/or second reflector can be found using equations (1-5) and (1-6).

Figure 6:
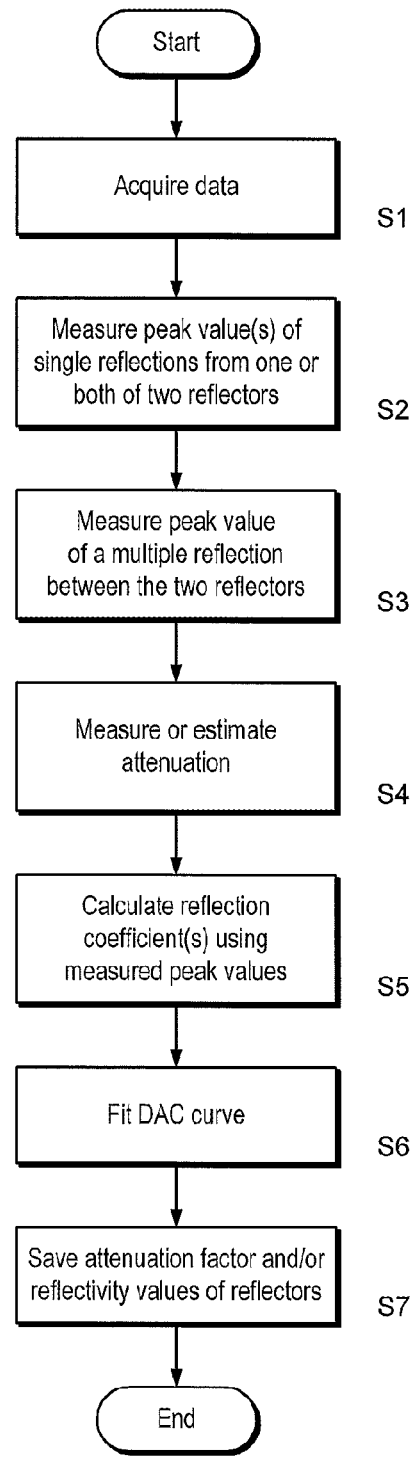
FIG. 6 is a process flow diagram of a method of determining the size of a reflector.

Referring to FIGS. 2 and 6, a pulse-echo measurement is carried out to acquire time trace data which includes a set of peaks including peaks corresponding to single reflections and peaks corresponding to the triple reflection (step S1). The peak amplitude(s) of single reflection(s) from one or both of two reflectors, i.e. $A_1$ and/or $A_2$, is (are) measured (step S2). The peak amplitudes of the triple reflections, i.e. $A_{121}$ and/or $A_{121}$, are also measured (step S3).

The reflection coefficient for the first reflector, i.e. $R_1$, is calculated by dividing the amplitude of the peak corresponding to the triple reflection, i.e. $A_{121}$, by the amplitude of the peak corresponding to a single reflection from the second reflector, i.e. $A_2$, and taking the square root (step S4). The attenuation factor, $\alpha$, can be set to zero or determined using one of the methods described later (step S4).

A similar calculation can be used to determine the reflection coefficient for the second reflector, i.e. $R_2$. Also, the values can be used to determine the amplitude of the outgoing wave, $A_0$.

Calibration involves fitting a distance amplitude correction (DAC) curve to one or more peaks corresponding to reflections from respective one or more reference features (such as welds) which are assumed to have the same reflectivity. The curve exhibits a characteristic fall off in amplitude attributable to attenuation. Thus, two features which have the same reflection coefficient, but which are located at different positions along a pipe, produce peaks having different peak amplitudes.

Once a DAC curve for a given reflectivity has been fitted to peaks whose reflectivity is known or determinable, attenuation can be found and further DAC curves for other values of reflectivity can be constructed. These other curves can be used to determine the reflectivity of other features.

Fitting a curve involves shifting and stretching the curve so that it intercepts the peak amplitudes. This can be done by an operator or by the computer system 11.

Figure 3:
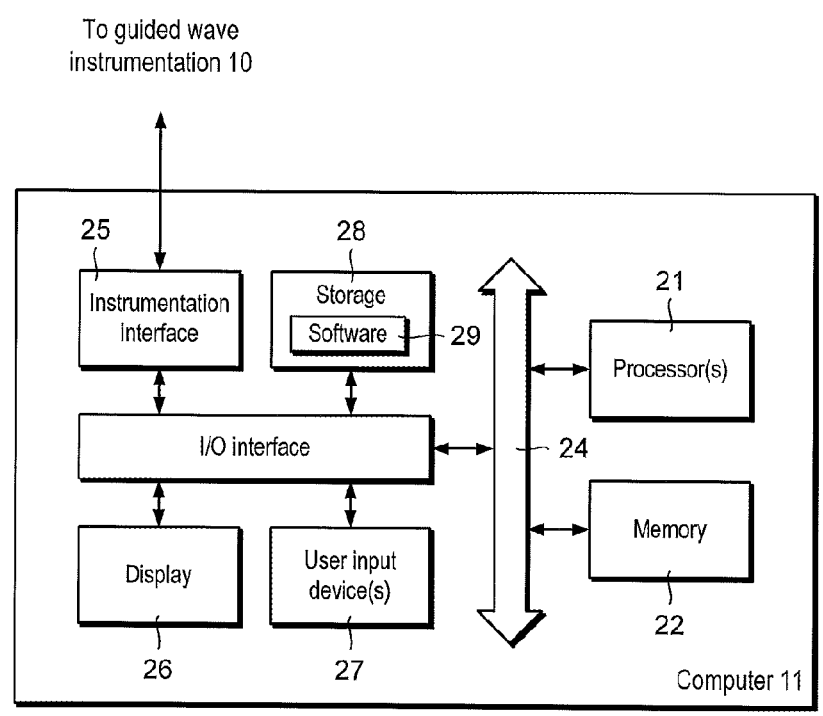
FIG. 3 is a schematic block diagram of a computer system used in the guided wave testing system shown in FIG. 2.

The sizing method hereinbefore described is used to calculate a reflection coefficient for a given feature. A DAC curve for the reflection coefficient can then be constructed and then fitted to the feature (step S6). The size of other features can then reported by the software with respect to this curve. Data, such as attenuation coefficients and reflection coefficients can be stored in storage 28 (FIG. 3) (step S7).

Figure 7:
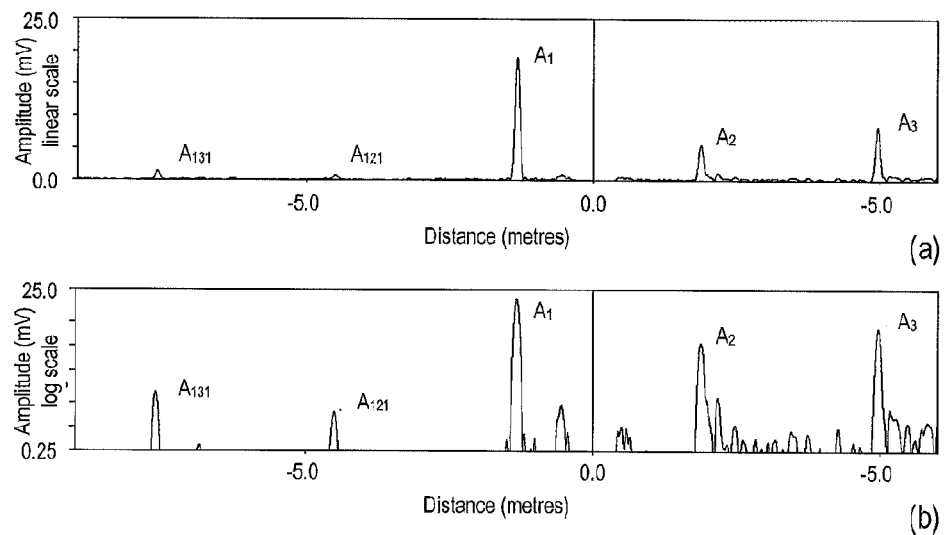
FIG. 7a is a linear plot of pulse-echo signal amplitude against distance for a guided wave test of a pipe, the plot showing reflections which are received from the same side of the pipe into which outgoing waves are sent.
FIG. 7b illustrates the same data shown in FIG. 7a except using a logarithmic scale.

FIG. 7 shows the result of a guided wave test using 20 kHz, torsional mode guided waves of an in-service pipe (not shown) having an outer diameter of 114.3 mm and a nominal wall thickness of 6.02 mm, and having a branch and two girth welds.

From the measurement, the following peak amplitudes can be measured, namely $A_{121} = 0.77$ mV, $A_1 = 18.99$ mV, $A_2 = 5.42$ mV. The peaks having amplitudes $A_1$ and $A_3$ correspond to welds and the peak having an amplitude $A_2$ corresponds to a branch.

Assuming that $\alpha = 0$, the reflection coefficient of the first feature (a weld) is $R_1 = 0.14$. The distance, measured from (the middle of) the transducer ring 3, of the first feature (a weld) is −1.32 m and for a second feature (branch) is +1.87 m. The distance to the reverberation is measured as −4.52 m. The reverberation is 3.20 m behind feature 1, which is approximately equal to the distance between feature 1 and 2.

$A_{121}$ and $A_{212}$ are related to each other by $A_{121}/A_{212} = (A_1)^2/(A_2)^2$.

Sizing of reflectors based on double reflections will be described.

The amplitudes $A_1$, $A_2$ and $A_{12}$ can be expressed as:

$$A_1 = A_0 R_1 \exp(-2\alpha |z_1|) \tag{2-1}$$

$$A_2 = A_0 R_2 \exp(-2\alpha |z_2|) \tag{2-2}$$

$$A_{12} = A_{21} = A_0 R_1 R_2 \exp(-2\alpha \{|z_1| + |z_2|\}) \tag{2-3}$$

These can be re-arranged as:

$$R_1 = \exp(2\alpha|z_1|) A_{12}/A_2 \quad (2\text{-}4)$$

$$R_2 = \exp(2\alpha|z_2|) A_{12}/A_1 \quad (2\text{-}5)$$

$$A_0 = A_1 A_2/A_{12} \quad (2\text{-}6)$$

Figure 8:
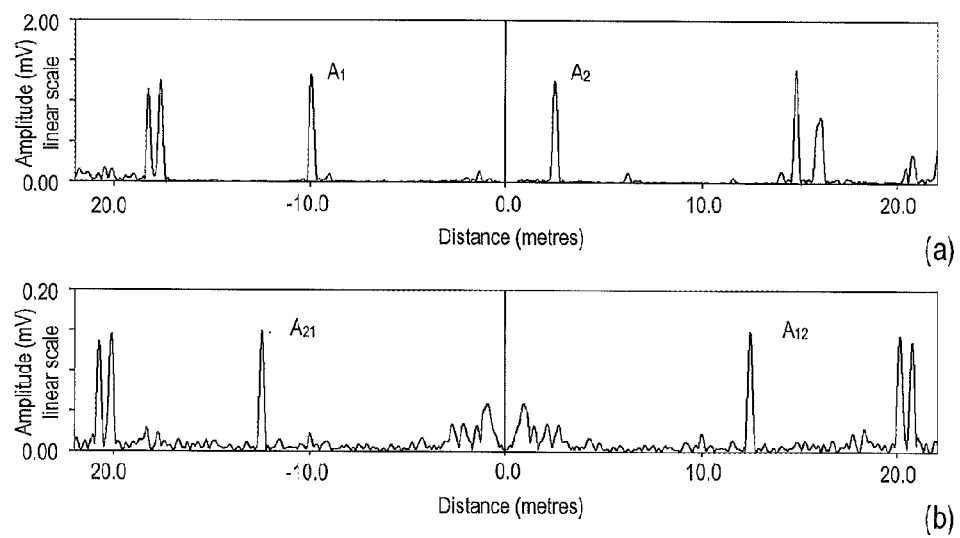
FIG. 8a is a plot of signal amplitude against distance for a guided wave test of another pipe, the plot showing reflections which are received from the same side of the pipe into which outgoing waves are sent.
FIG. 8b is a plot of signal amplitude against distance for a guided wave test of another pipe, the plot showing reflections which are received from the opposite side of the pipe into which outgoing waves are sent.

FIG. 8 shows the result of a guided wave test using 36 kHz, torsional mode guided waves of an in-service pipe (not shown) having an outer diameter of 406.4 mm and a nominal wall thickness of 6.35 mm, and having, amongst other features, two girth welds.

From the measurement, the following peak amplitudes can be measured, namely $A_{21} = A_{12} = 0.15$ mV, $A_1 = 1.34$ mV and $A_2 1.25$ mV.

Assuming that $\alpha = 0$, the first reflection coefficient, $R_1$, is 0.14 and the second reflection coefficient, $R_2$, is 0.11. The first feature is −9.96 m from the transducer ring position and the second feature is +2.51 m from the transducer ring. The distance between the first and second features is 12.45 m, which is equal to the distance where the reverberation occurs.

Determining Attenuation

As explained earlier, the attenuation factor, $\alpha$, can be set to zero if it is small. The exponential term containing the attenuation factor then has a value of one. This approximation may be appropriate also when the distance between two reflectors is small, e.g. a few meters.

However, the attenuation factor can be found at step S4 (FIG. 6), for example, in one of two ways.

In a first method, the transducer ring 3 is moved a distance, $\Delta z$, between two reflectors and the change in scale of the guided wave signals is observed. In order for this approach to be independent of the coupling of the transducer ring at the two test positions, the guided wave signals of two reflectors located on either side of the transducer ring are used:

$$A_1(0) = A_0 R_1 \exp(-2\alpha|z_1|) \quad (3\text{-}1)$$

$$A_2(0) = A_0 R_2 \exp(-2\alpha|z_2|) \quad (3\text{-}2)$$

$$A_1(\Delta z) = A_0(\Delta z) R_1 \exp(-2\alpha(|z_1|+\Delta z)) \quad (3\text{-}3)$$

$$A_2(\Delta z) = A_0(\Delta z) R_2 \exp(-2\alpha(|z_2|-\Delta z)) \quad (3\text{-}4)$$

where $\Delta z$ is the distance between measurements.

Then $$[A_1(\Delta z)/A_1(0)]/[A_2(\Delta z)/A_2(0)] = \exp(-4\alpha \Delta z) \quad (3\text{-}5)$$

from which the attenuation, $\alpha$, can be calculated.

If the attenuation is found to be negligible and/or the distance between the two reflectors is small, then the attenuation value may be set to zero.

In a second method, the DAC curves are fitted to two or more features with assumed equal reflectivity, normally a series of girth welds.

Attenuation may also be set to a value based on experience.

Clamping Effect of a Row of Transducers

Two rows of transducers 5 can themselves act as clamps on the pipe and, therefore, reflect guided waves. Thus, a guided wave passing through a row of transducers can reflect part of the wave and reduce the transmission amplitude.

Figure 9:
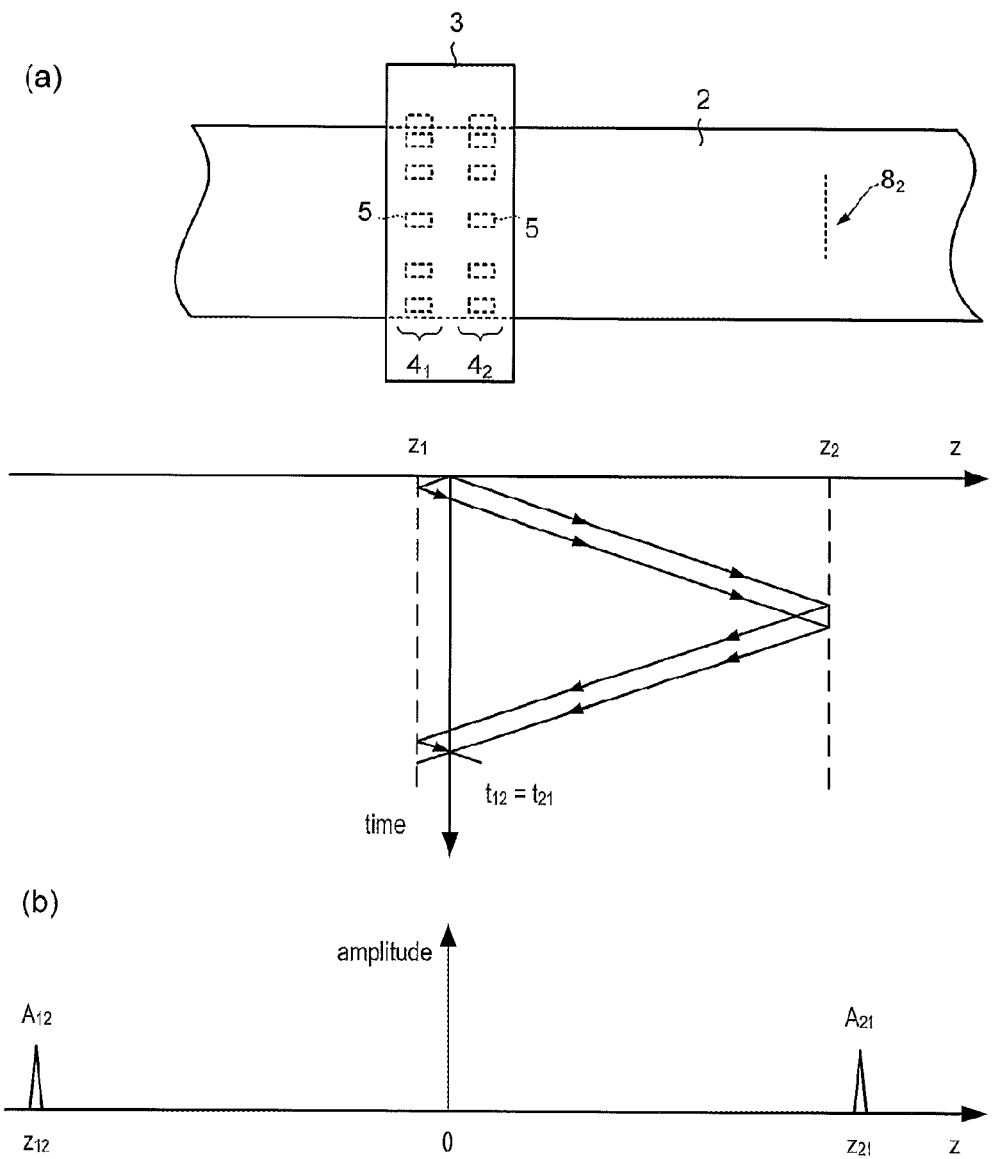
FIG. 9 illustrates propagation of guided waves in pipe where a row of transducers acts as a reflector.

Referring to FIG. 9, the effect that a row $4_1$, $4_2$ of transducers 5 can have is shown. As shown in FIG. 9, a guided wave can be reflected from a first row of transducers. Thus, the row of transducers can serve as a reflector and, therefore, its reflection coefficient can be determined. Notwithstanding this, the effect tends to be negligible for normal applications because reflection is usually small and, therefore, the error due to transmission loss is small. For example, FIG. 8 has a pair of peaks at about ±10 m which is the signal arising from the first reflector and one of the rows of transducers.

Where the reflection from a row of transducers can be neglected, the arrangements can be used to detect and size features, such as defects, that are located in the near field (i.e. in a length of pipe either side of the transducer ring 3 in which the true amplitude of reflections is underestimated) or in the dead zone (i.e. in a length of pipe either side of the transducer ring 3 equivalent to the length of the transmitted signal where reflections cannot be obtained), similar to determining the reflection coefficient of a transducer row.

Other Arrangements

Different reverberation paths than the ones considered above may possibly be used to calculate the reflection coefficients. In particular, these can include paths where both reflectors are on one side of the transducer, rather than described above on opposite sides of the transducer. In tube testing, the presence of two ends with refection coefficients close to 1 leads to characteristic successive reverberations along different paths. These reverberated reflections add constructively as they undergo equal phase changes each time the signal reverberates between the ends and any features in between. Observing these reverberations instead of or in addition to the direct signal can be used to increase sensitivity to small defects. Again, an appropriate calculation using the reverberated signals can be used to calibrate and size the features of interest.

Reflectors Located on the Same Side of the Transducer Ring

In the examples given earlier, the features (i.e. reflectors) are located on opposite sides of the transducer ring 3 (FIG. 2). The sizing and calibration method can be used even when features are located on the same side of the transducer ring.

Figure 10:
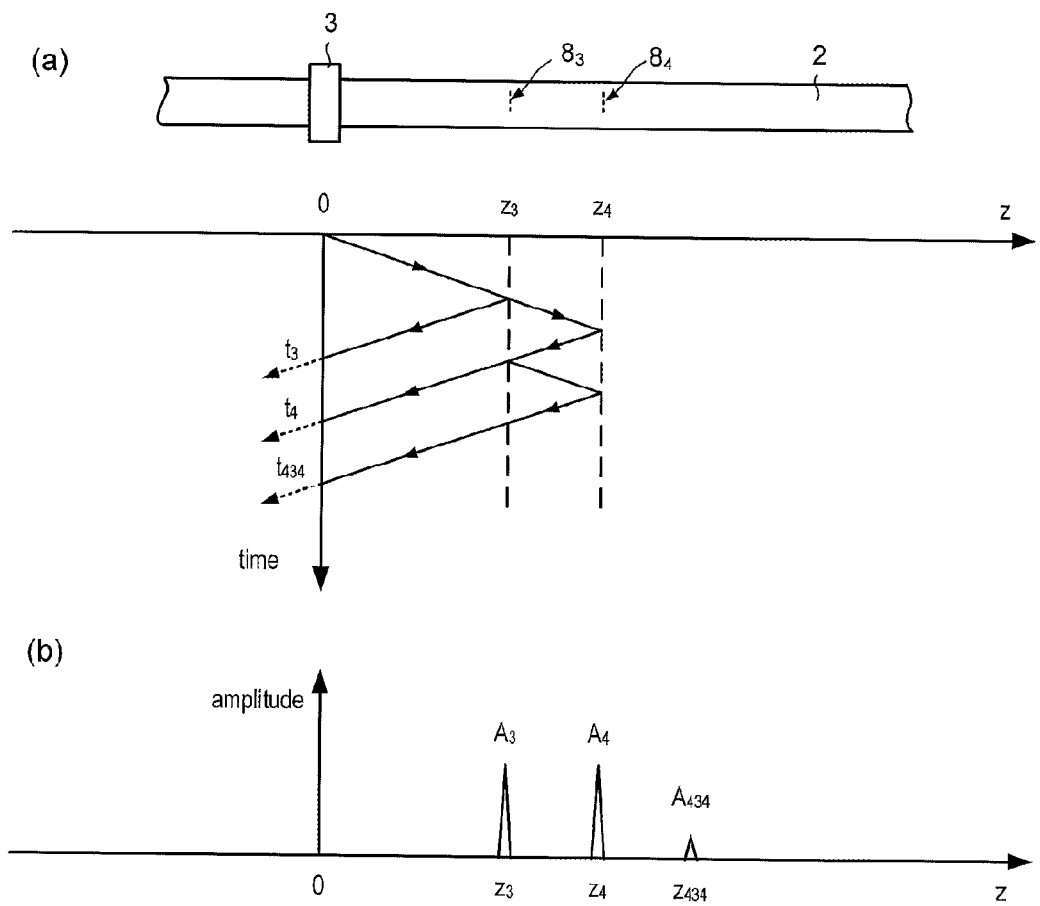

Referring to FIG. 10a, the pipe 2 is shown having third and fourth reflectors $8_3$, $8_4$ located on the same side of the transducer ring 3. The transducer ring 3 is used to excite a guided wave which propagates forwards. The guided waves are reflected by the reflectors $8_3$, $8_4$ and the reflected waves are detected by the transducer ring 3.

The transducer ring 3 receives third and fourth direct pulse-echo (i.e. single-reflection) signals reflected from the first and second reflectors $8_3$, $8_4$ respectively and having paths z: $0 \to z_3 \to 0$ and z: $0 \to z_4 \to 0$. The first and second direct pulse-echo signals have peak amplitude values $A_3$ and $A_4$ respectively.

The transducer ring 3 receives a triple-reflection signal which has been reflected first by the fourth reflector $8_4$, then by the third reflector $8_3$ and then again by the fourth reflector $8_4$, i.e. a path z: $0 \to z_4 \to z_3 \to z_4 \to 0$. In this case, the reverberated signal has amplitude $A_{434}$ and is received by the transducer ring 3 from the direction of the third and fourth reflectors $8_3$, $8_4$.

FIG. 10b is an amplitude—distance plot showing peaks in amplitude corresponding to single and triple reflections. The characteristic distances at which the signals appear can be used to identify reverberation echoes and distinguish them from real reflectors.

The reflection coefficients $R_3$ and $R_4$ for third and fourth reflectors can be calculated as follows. The amplitudes $A_3$, $A_4$ and $A_{434}$ can be expressed as:

$$A_3 = A_0 R_3 \exp(-2\alpha|z_3|) \quad (3\text{-}1)$$

$$A_4 = A_0 R_4 (1 - R_3^2) \exp(-2\alpha|z_4|) \quad (3\text{-}2)$$

$$A_{434} = A_0 R_4^2 R_3 (1 - R_3^2) \exp(-2\alpha(2|z_4| - |z_3|)) \quad (3\text{-}3)$$

where is $\alpha$ an attenuation factor which can be zero or a positive non-zero number (i.e. $0 \leq \alpha$) and $A_0$ is the amplitude of the outgoing wave.

Equations (3-1), (3-2) and (3-3), for example, can be re-arranged as:

$$R_3 = 1/\mathrm{sqrt}(A^* + 1) \quad (3\text{-}4)$$

$$R_4 = \exp(2\alpha(|z_4| - |z_3|)) \mathrm{sqrt}(A^* + 1) A_4 / (A_3 A^*) \quad (3\text{-}5)$$

$$A_0 = \exp(2\alpha|z_3|) A_3 \, \mathrm{sqrt}(A^* + 1) \quad (3\text{-}6)$$

where $A^* = A_4^2 / (A_3 A_{434})$. $R_3$ can be determined without knowledge of attenuation. The reflection coefficient $R_3$ (and/or $R_4$) for the third and/or fourth reflectors can be found using equations (3-4) and (3-5). The amplitude of the outgoing wave, $A_0$, can also be found.

It will be appreciated that many modifications can be made to the embodiments hereinbefore described.

Discrete or segmented piezoelectric transducers need not be used. For example, transducers based on magneto-restrictive or Lorentz force can be used. In the case of magneto-restrictive transduction, the transducer can take the form of a single strip of magneto-restrictive arranged around the circumference of the pipe. In some embodiments, for example using transducers which employ exciting waves via the Lorenz force, the transducers need not be in contact with the pipe.

Higher frequency guided waves, for example up to 2 MHz, can be used.

Other guided waves modes, e.g. longitudinal mode, can be used.

Reflectors need not be adjacent. For example, another reflector (or several reflectors) can lie between two reflectors.

Reflection coefficients (or other parameters) can be found using even-numbered reflections and odd-numbered reflections, and can be combined (e.g. by taking the average) to obtain a combined value, e.g. an average, of reflection coefficient.

Reflection coefficients (or other parameters) can be found using multiple reflections without using any single reflections or using fewer single reflections. For example, instead of using single reflections from the reflectors, triple reflections may be used. These can then be used together with double (or other even-numbered) reflections to obtain reflection coefficients. Alternatively, for example, a single reflection, a triple reflection used instead of a single reflection and a double reflection can be used. This can be used when one or more single reflections cannot be observed or measured.

The invention claimed is:

1. A computer-implemented method of processing signals and calibrating a guided wave test, the method comprising:
    receiving signals acquired during guided wave testing of an elongate member, the guided wave testing including first and second guided waves generated in the elongate member on first and second, opposite sides respectively of a transducer ring, the first and second guided waves propagated in first and second opposite directions respectively, the guided waves reflected by reflectors in the elongate member and reflected guided waves detected;
    determining at least one reflection coefficient or a parameter for calibrating a guided wave test in dependence upon reflections from the reflectors which include a single reflection from a first reflector on the first side, a single reflection from a second reflector on the second side and a multiple reflection from the first and second reflectors,
    wherein determining the parameter for calibrating a guided wave test comprises:
        calculating an amplitude, $A_0$, of the first and second guided waves, wherein:

$$A_0 = \mathrm{sqrt}((A_1)^2 A_2 / A_{121})$$

wherein:
            $A_1$ is a peak value of a peak corresponding to the single reflection of the first guided wave from the first reflector,
            $A_2$ is a peak value of a peak corresponding to the single reflection of the second guided wave from the second reflector, and
            $A_{121}$ is a peak value of a peak corresponding to a triple reflection of the first guided wave from, in order, the first reflector, the second reflector and the first reflector;
    and
    calibrating the guided wave test on the elongate member by fitting a distance amplitude correction (DAC) curve using the amplitude, $A_0$.

2. A computer-implemented method according to claim 1, wherein the first and second guided waves comprise respective pulses and the amplitudes are amplitudes of peaks corresponding to respective reflections of the pulses.

3. A computer-implemented method according to claim 1, comprising:
    transmitting signals to at least two sets of transducers spaced apart along the elongate member;
    receiving signals from at least two sets of transducers spaced apart along the elongate member; and
    extracting signal contributions corresponding to even-numbered reflections.

4. A computer-implemented method according to claim 3, the method comprising:
    displaying a plot using the extracted signal contributions.

5. A computer-implemented method according to claim 1, wherein the second reflector used to determine the reflection coefficient or parameter is located outside a dead zone or near field and the first reflector used to determine a reflection coefficient or parameter is located inside the dead zone or near field.

6. A computer-implemented method, comprising:
    generating the first and second guided waves in the elongate member;
    acquiring signals from transducers coupled to the elongate member; and
    processing the signals according to claim 1.

7. A non-transitory computer-readable medium storing a computer program which, when executed by a computer, causes the computer to perform a method according to claim 1.

8. Apparatus configured to perform the method according to claim 1, the apparatus comprising: transducers for generating at least one guided wave in an elongate member, and instrumentation for generating a set of signals for driving the transducers and receiving signals generated by the transducers.

9. Apparatus according to claim 8, wherein the computer and instrumentation are unitary.

10. A computer-implemented method according to claim 1, wherein the parameter for calibrating the guided wave test is the amplitude, $A_0$, of first and second guided waves.

11. A computer-implemented method of processing signals and calibrating a guided wave test, the method comprising:
receiving signals acquired during guided wave testing of an elongate member, the guided wave testing including first and second guided waves generated in the elongate member on first and second, opposite sides respectively of a transducer ring, the first and second guided waves propagated in first and second opposite directions respectively, the guided waves reflected by reflectors in the elongate member and reflected guided waves detected;
determining at least one reflection coefficient or a parameter for calibrating a guided wave test in dependence upon reflections from the reflectors which include a single reflection from a first reflector on the first side, a single reflection from a second reflector on the second side and a multiple reflection from the first and second reflectors,
wherein determining the parameter for calibrating a guided wave test comprises:
calculating an amplitude, $A_0$, of first and second guided waves, wherein:

$$A_0 = A_1 A_2 / A_{12}$$

wherein:
$A_1$ is a peak value of a peak corresponding to the single reflection of the first guided wave from the first reflector,
$A_2$ is a peak value of a peak corresponding to the single reflection of the first guided wave from a second reflector, and
$A_{12}$ is a peak value of a peak corresponding to a double reflection of the first guided wave from the first reflector and then the second reflector;
and,
calibrating the guided wave test on the elongate member by fitting a distance amplitude correction (DAC) curve using the amplitude, $A_0$.

12. A computer-implemented method according to claim 11, wherein the first and second guided waves comprise respective pulses and the amplitudes are amplitudes of peaks corresponding to respective reflections of the pulses.

13. A computer-implemented method according to claim 11, comprising:
transmitting signals to at least two sets of transducers spaced apart along the elongate member;
receiving signals from at least two sets of transducers spaced apart along the elongate member; and
extracting signal contributions corresponding to even-numbered reflections.

14. A computer-implemented method according to claim 11, wherein the second reflector used to determine the reflection coefficient or parameter is located outside a dead zone or near field and the first reflector used to determine a reflection coefficient or parameter is located inside the dead zone or near field.

15. A computer-implemented method, comprising:
generating the first and second guided waves in the elongate member;
acquiring signals from transducers coupled to the elongate member; and
processing the signals according to claim 11.

16. A computer-implemented method according to claim 11, the method comprising:
displaying a plot using the extracted signal contributions.

17. A non-transitory computer-readable medium storing a computer program which, when executed by a computer, causes the computer to perform a method according to claim 11.

18. Apparatus configured to perform the method according to claim 11, the apparatus comprising: transducers for generating at least one guided wave in an elongate member, and instrumentation for generating a set of signals for driving the transducers and receiving signals generated by the transducers.

19. Apparatus according to claim 18, wherein the computer and instrumentation are unitary.

20. A computer-implemented method according to claim 11, wherein the parameter for calibrating the guided wave test is the amplitude, $A_0$, of first and second guided waves.

21. A computer-implemented method of processing signals and calibrating a guided wave test, the method comprising:
receiving signals acquired during guided wave testing of an elongate member, the guided wave testing including first and second guided waves generated in the elongate member on first and second, opposite sides respectively of a transducer ring, the first and second guided waves propagated in first and second opposite directions respectively, the guided waves reflected by reflectors in the elongate member and reflected guided waves detected;
determining at least one reflection coefficient or a parameter for calibrating a guided wave test in dependence upon reflections from the reflectors which include a single reflection from a first reflector on the first side, a single reflection from a second reflector on the second side and a multiple reflection from the first and second reflectors,
wherein determining the at least one reflection coefficient includes:
calculating a reflection coefficient, $R_1$, of the first reflector and/or a reflection coefficient, $R_2$, of the second reflector, wherein:

$$R_1 = \exp(2\alpha |z_1|) \operatorname{sqrt}(A_{121}/A_2)$$

$$R_2 = \exp(2\alpha |z_2|) \operatorname{sqrt}(A_{121} A_2 / (A_1)^2)$$

wherein:
$A_1$ is a peak value and $z_1$ is the peak position of a peak corresponding to the single reflection of the first guided wave from the first reflector,
$A_2$ is a peak value and $z_2$ is the peak position of a peak corresponding to the single reflection of the second guided wave from the second reflector,
$A_{121}$ is a peak value of a peak corresponding to a triple reflection of the first guided wave from, in order, the first reflector, the second reflector and the first reflector, and
$\alpha$ is an attenuation coefficient having a value zero or a positive non-zero number;
and,
calibrating the guided wave test on the elongate member by fitting a distance amplitude correction (DAC) curve using the reflection coefficient, $R_1$, of the first reflector and/or the reflection coefficient, $R_2$, of the second reflector.

22. A computer-implemented method of processing signals and calibrating a guided wave test, the method comprising:
    receiving signals acquired during guided wave testing of an elongate member, the guided wave testing including first and second guided waves generated in the elongate member on first and second, opposite sides respectively of a transducer ring, the first and second guided waves propagated in first and second opposite directions respectively, the guided waves reflected by reflectors in the elongate member and reflected guided waves detected;
    determining at least one reflection coefficient or a parameter for calibrating a guided wave test in dependence upon reflections from the reflectors which include a single reflection from a first reflector on the first side, a single reflection from a second reflector on the second side and a multiple reflection from the first and second reflectors,
    wherein determining the at least one reflection coefficient includes:
        calculating a reflection coefficient, $R_1$, of the first reflector and/or a reflection coefficient, $R_2$, of the second reflector, wherein:
        $$R_1 = \exp(2\alpha|z_1|)A_{12}/A_2$$
        $$R_2 = \exp(2\alpha|z_2|)A_{12}/A_1$$
        wherein:
            $A_1$ is a peak value and $z_1$ is the peak position of a peak corresponding to the single reflection of the first guided wave from the first reflector,
            $A_2$ is a peak value and $z_2$ is the peak position of a peak corresponding to the single reflection of the second guided wave from the second reflector,
            $A_{12}$ is a peak value of a peak corresponding to a double reflection of the first guided wave from the first reflector and then the second reflector, and
            $\alpha$ is an attenuation coefficient having a value zero or a positive non-zero number;
    and,
    calibrating the guided wave test on the elongate member by fitting a distance amplitude correction (DAC) curve using the reflection coefficient, $R_1$, of the first reflector and/or the reflection coefficient, $R_2$, of the second reflector.

* * * * *